United States Patent [19]
Haverstock

[11] 3,933,158
[45] Jan. 20, 1976

[54] SKIN CLOSURE MEANS

[76] Inventor: Charles B. Haverstock, 44 Frederick Lane, Glendale, Mo. 63122

[22] Filed: Feb. 15, 1974

[21] Appl. No.: 442,784

[52] U.S. Cl. ............................................... 128/335
[51] Int. Cl.² .......................................... A61B 17/08
[58] Field of Search ........................... 128/155–156, 128/168–171, 327, 334 R, 334 C, 335; 24/155 SD, 201 C, 203, 205 R, 205.1; 27/21; 150/3, 5, 42

[56] References Cited
UNITED STATES PATENTS

| | | | |
|---|---|---|---|
| 2,409,489 | 10/1946 | Hurt | 150/3 |
| 2,752,921 | 7/1956 | Fink | 128/334 R |
| 3,346,883 | 10/1967 | Ersek | 150/3 |
| 3,516,409 | 6/1970 | Howell | 128/335 |
| 3,517,702 | 6/1970 | Mueller et al. | 24/201 C |
| 3,568,276 | 3/1971 | Morgan | 128/335 X |
| 3,698,395 | 10/1972 | Hasson | 128/335 |

Primary Examiner—Robert W. Michell
Assistant Examiner—Rick Opitz
Attorney, Agent, or Firm—Charles B. Haverstock

[57] ABSTRACT

Improvements in skin closures includng a device for uniting and holding separable closure members and skin portions attached thereto accurately together and to prevent separation thereof by forces which might otherwise cause the united members to separate. The subject construction also includes portions for accurately aligning and holding the separated edges of a skin wound or incision together during healing in such a way as to minimize or prevent the formation of scar tissue. The subject closures are easy to apply quickly and accurately even under adverse conditions such as in first-aid treatment during emergencies, under disaster and wartime conditions, in emergency wards, in field, forest and wilderness situations and also under more controlled conditions such as in operating rooms and doctors' offices particularly as the final step in completing a skin closure.

20 Claims, 20 Drawing Figures

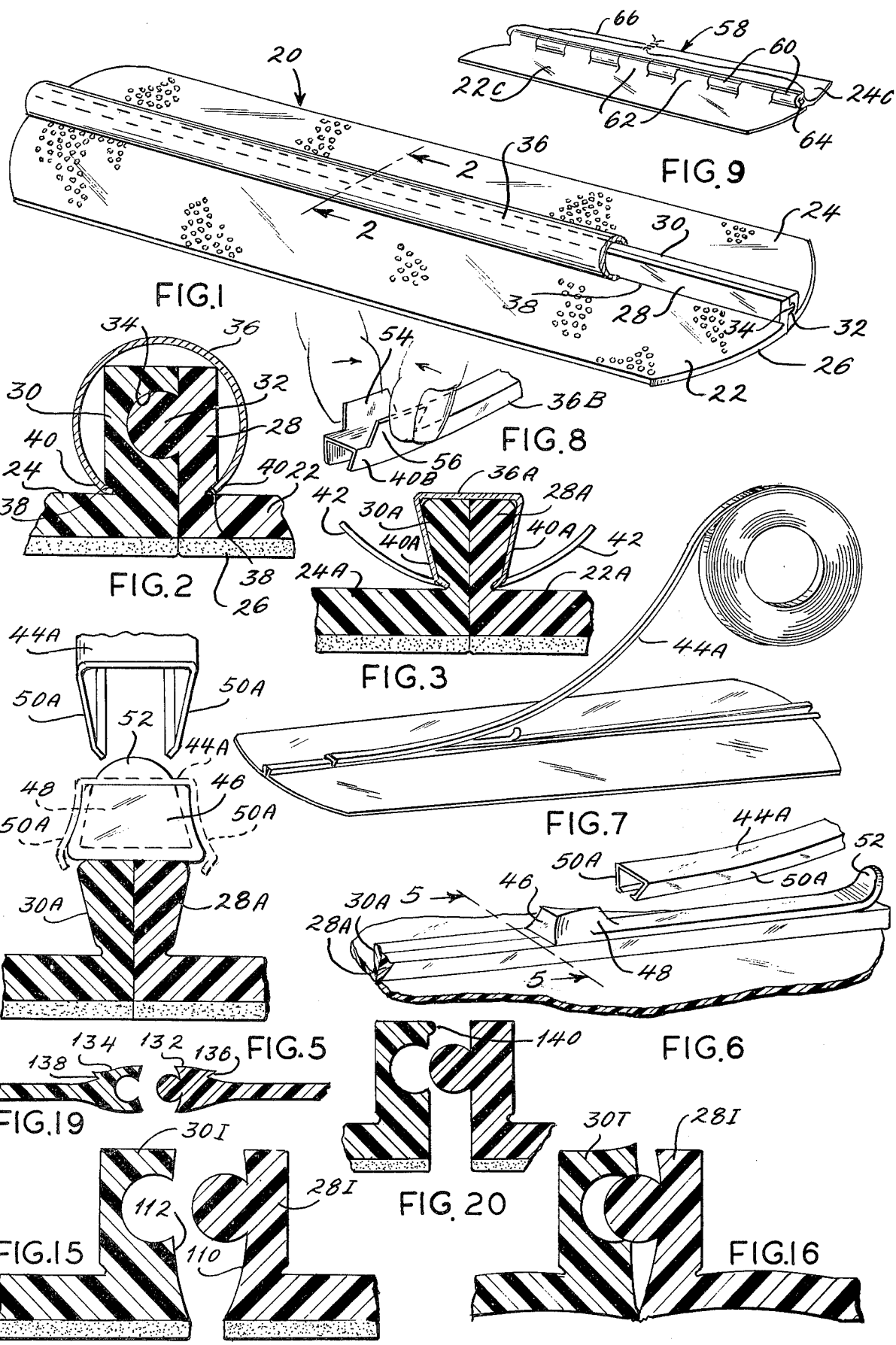

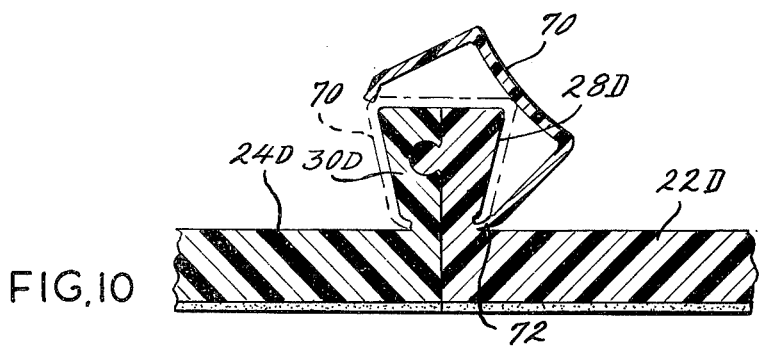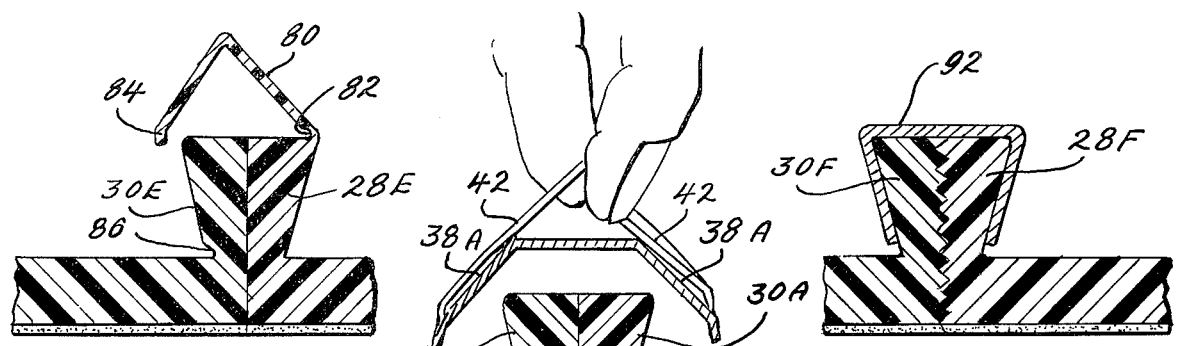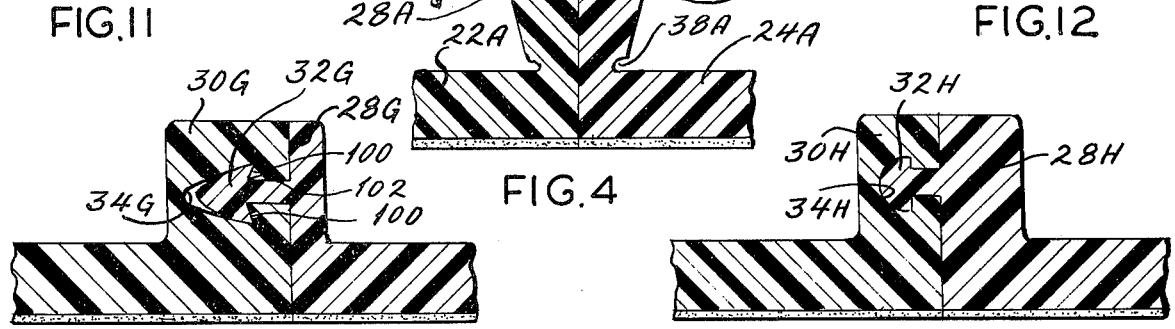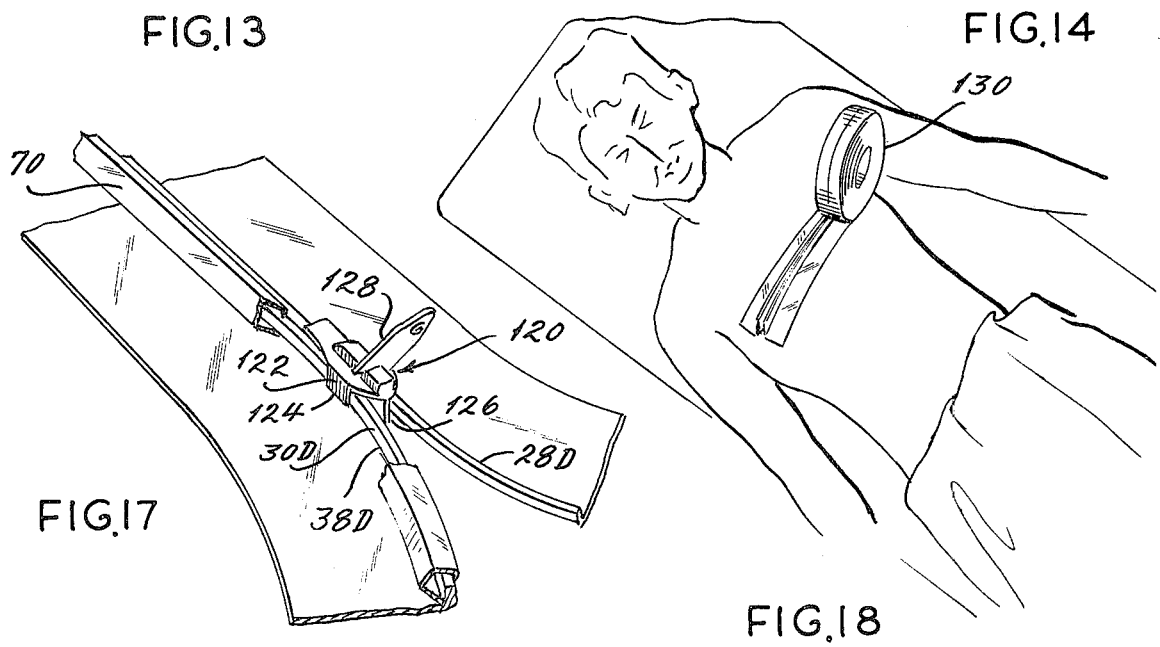

SKIN CLOSURE MEANS

In my U.S. Pat. No. 3,863,640 I disclosed the idea of providing a zipper or zipper-like bandage construction or skin closure by which the separated side edges of a skin injury, wound, incision, laceration or the like can be accurately aligned, closed and held in the most advantageous position to facilitate healing with a minimum of scar formation. Such devices are particularly useful in situations where there is no access to medical assistance, and the prior constructions also have applications in surgical procedures or under emergency medical treatment procedures where time is limited and where other suturing means are unavailable. The present means may even be superior to suturing in many cases. They are also useful in emergency situations such as in catastrophy and in wartime where there is a great need to be able to quickly and accurately close injuries or skin separations to prevent loss of blood and for other purposes readily apparent to those skilled in emergency treatment. Thus the present construction substantially reduces or eliminates the need for suturing and is also useful as a means of preventing the formation of scar tissue. It is recognized, however, that in some surgical procedures especially where deep incisions are made that some subcutaneous suturing may be desired, but even in these situations the ability to be able to quickly and accurately close the incision at the skin surface may be brought about by use of closure means such as disclosed in this and in my previous copending application.

It is recognized that slide fastener type means, especially those that include male and female plastic or plastic like members, when pressed or slipped together by some form of zipper means may tend to separate when excessive lateral forces are exerted on the joined members thus causing them to open. This can also occur under stress such as movements of a bedpatient, clothes rubbing on the closure or fidgeting or pulling at the closure by the injured person. This is highly undesirable especially when the zipper means are being used to align and hold a wound or separation together, therefore, the present case discloses improved closure means to minimize the chance for a bandage construction or closure such as disclosed in my prior application to come apart after being applied. Some forms of the present invention additionally have application during actual surgical procedures.

It is therefore a principal object of the present invention to reduce or minimize the possibility that skin closure means such as disclosed in my U.S. Pat. No. 3,863,640 when used for closing a wound, incision or laceration will undesirably open or separate under stress.

Another object is to provide auxiliary means which are relatively easy to install on zipper-type skin closure devices or the like to prevent separation of components thereof when they have been joined.

Another object is to improve the healing conditions between separated skin areas along a break or tear in the skin.

Another object is to provide improved means for holding together the edge portions of a separable bandage or bandage like construction.

Another object is to reduce or eliminate the need for suturing, particularly cutaneous suturing in medicosurgical procedures.

Another object is to minimize the formation of scar tissue and keloiding in the closing of wounds, incisions, lacerations and other skin separations.

Another object is to teach the construction of skin closure means which are adaptable to be made in any lengths and widths and which can be trimmed or cut to facilitate use as needed or desired depending on the nature, location and contour of the skin at the wound to be closed.

Another object is to teach the construction and operation of zipper-type skin closure means which can be closed and reopened and reclosed as required.

Another object is to provide skin closure means which are particularly adaptable to use in emergency situations, which means require no special medical skill or training to apply.

Another object is to teach the construction of skin closure means which can be applied and closed without requiring any special tools.

Another object is to provide an effective skin closure which can be removed when it has served its purpose like an ordinary adhesive bandage.

Another object is to provide additional options for closing wounds or the like.

These and other objects and advantages of the present invention will become apparent after considering the following detailed specification which discloses several different embodiments of the subject construction in conjunction with the accompanying drawings, wherein:

FIG. 1 is a perspective view of a two part skin closure construction wherein severable portions thereof are joined and held together by means constructed according to one form of the present invention;

FIG. 2 is an enlarged cross-sectional view taken along line 2–2 of FIG. 1;

FIG. 3 is a cross-sectional view similar to FIG. 2 but showing a modified form of the subject closure and holder means;

FIG. 4 is an enlarged cross-sectional view showing one way for applying the closure and holding means of FIG. 3;

FIG. 5 is an enlarged cross-sectional view showing another modified form of the subject closure and holder means and a modified way of installing same;

FIGS. 6 and 7 are perspective views further illustrating application of the closure and holding means of FIG. 5;

FIG. 8 is a perspective view showing another modified form of the subject skin closure means;

FIG. 9 is a perspective view of another modified form of the skin closure means;

FIG. 10 is a cross-sectional view similar to FIG. 3 but showing another form of skin closure means; the device being shown in solid outline before completion of the closure and in dotted outline after installation;

FIGS. 11–14 are cross-sectional views showing other embodiments of the subject closure means;

FIGS. 15 and 16 are cross-sectional views of yet another form of the subject means;

FIG. 17 is a perspective view of an embodiment similar to that shown in FIG. 10 but wherein a zipper member is positioned for movement in one direction to close the subject means and in the opposite direction to open and separate the closure means;

FIG. 18 shows a roll of the subject closure means which can be cut off at any desired and lengths as desired;

FIGS. 19 and 20 are cross-sectional views showing still other shapes for the subject closure;

Referring to the drawings more particularly by reference numbers and wherein like numerals refer to like parts, number 20 in FIG. 1 indicates skin closure means constructed according to one embodiment of the subject invention. The closure means 20 includes two separable portions 22 and 24 preferably made of a relatively flexible material, preferably a plastic or plastic-like material, each of which is constructed to be positioned having one side edge thereof extending along one side of a wound, incision, or other skin opening or separation to be closed. The two portions 22 and 24 have adhesive means for attaching it to the skin adjacent to the separated edges of the wound. The adhesive surface is indicated generally by number 26 and preferably extends over the entire skin contacting surfaces rather than having a gauze or other layer of nonadhesive material in contact with the wound as in usual bandage constructions. When the portions 22 and 24 are applied to the separated edges of the wound there will be usually some space between them corresponding to the distance between the separated edges of the wound, incision or the like. The portion 22 has formed or attached thereto means 28 shown as a flange member having a bead or rib 32 which forms the male portion of the subject closure, and the portion 24 has means 30 shown as a flange member having a groove or recess 34 which forms the female portion of the construction for cooperatively receiving the rib 32. The male and female means on the portions 28 and 30 are constructed so that when they are pressed together by finger pressure or by other means such as a movable zipper member they will become engaged with each other and will thereafter resist coming apart. These members are preferably formed of a relatively resilient but also relatively stiff plastic or plastic like material so that they snap together and resist separation. Similar means are used on plastic slide zippers on brief cases, plastic bags, and so forth. As reinforcement in order to assure that the flange portions 28 and 30 do not separate or come apart undesirably, a split resilient tube member 36 (FIGS. 1 and 2) is positioned extending over and around the attached flanges 28 and 30 as clearly shown in FIG. 2. The portions 28 and 30 may also have notches or indentations 38 formed at the bases thereof also as shown in FIG. 2, and these notches cooperatively receive the edge portions 40 of the split tubular member 36 when it is installed to keep it in place and to prevent it from sliding or easily being pulled off. In order to position the tubular member 36 on the portions 28 and 30 it may be necessary to spread apart the free edges 40 thereof so that the tube will resiliently engage the opposite sides of the flanges 28 and 30 and hold them together. This is usually easy to accomplish simply by bending the tube 36 to start the separation, although a special tool can be provided for this purpose as will be explained.

FIG. 3 shows another embodiment of the subject construction wherein the two portions 28A and 30A of the subject members 22A and 24A are each positioned inside of another resilient tube or channel shaped member 36A which is supported by conjoined portions 28A and 30A. In this construction the members are held in position by means of the closure member 36A which is positioned thereon by spreading apart the lower leg portions 40A using attached flaps 42, which flaps are pulled apart or pinched to open the member 36A and to start to position it on the abutting members 28A and 30A as shown in FIG. 4. Once the closure member is started at one end it is usually a simple matter to complete the application by pressing down and applying thumb or other pressure beginning at the end that has been started. It may also be possible to slide the member 36A on.

FIG. 5 shows a member 44A being applied using a simple tool 46, the details of which are shown in FIGS. 6 and 7. The tool 46 has a portion formed with cam surfaces 48 which engage the closure member 44A as shown and spread the leg portions thereof including the leg portions 50A apart, as shown in FIG. 5. Thereafter the tool is moved or pulled by its operator portion 52 which is attached to the cam portion 48 to spread the leg portions as they are applied to the closure. In so doing the member 44A will slip down over the adjacent portions 28A and 30A of the closure means to resiliently hold them together as clearly shown in FIG. 7. The application is completed while applying downward pressure on the closure member 44A as the tool is moved to the right as shown in FIGS. 6 and 7. The joined portions 28A and 30A may have a construction as shown in FIGS. 3 and 4 or may have cooperating bead and groove means as in the construction of FIGS. 1 and 2 as desired depending on the rigidity or flexibility of the members involved and the desired holding strength or the like.

FIG. 8 shows another embodiment 36B of a closure member which is similar to the closure member 36A. The member 36B differs from the member 36A mainly because of the way its leg portions are spread apart during installing. This construction has two upwardly extending flanges 54 and 56 which are extensions of the leg portions of the closure 36B and these flanges can be easily pressed together to spread the leg portions 40B apart at the start of an installation. Once the member 36B is installed the flanges can be cut off, if desired, to prevent them from catching on things.

FIG. 9 shows another embodiment 58 of the subject skin closure wherein the two separable portions 22C and 24C have alternate interlocking tubular side edge portions 60 and 62. The members 22C and 24C are adhesively applied to the skin as in the above constructions, and thereafter they are brought together by moving them to cooperating positions in which the openings 64 through the portions 60 and 62 are in alignment. In this position a rod, wire or cord 66 is passed through all of the aligned openings 64 in a manner similar to inserting the hinge pin in a hinge assembly to hold the members together. With this construction the pin or cord 66 can be relatively easily removed to re-open the injury for inspection and or medicating if desired. In the construction as shown the wire 66 has its ends twisted to keep it in position.

FIG. 10 shows an embodiment of the subject construction wherein the two separable portions 22D and 24D each has a flange portion 28D and 30D respectively which include male and female bead and groove portions which cooperate in a manner similar to that already described. In this construction the member 22D is also shown having an integral secondary means in the form of a multi-wall member 70 which is connected to one of the members 22 or 24 by a relatively thin bendable portion 72. When the flanges 28D and 30D are joined together as indicated above the closure member 70, shown having three connected wall portions, is simply pressed down and snapped into position completing the closure as shown in dotted outline.

FIG. 11 shows another embodiment of a skin closure similar to that shown in FIG. 10 but wherein the form of multi-wall closure means 80 has only two wall portions instead of three, and is connected to flange member 28E at a thin bendable wall portion 82 located as shown rather than being attached at the root of the member to be joined as in the FIG. 10 construction. In this construction the flange portions 28E and 30E are brought together to the position shown and the wall portion 80 is moved down into snapped together engagement with the free edge portion 84 of the wall member 80 engaged in groove 86 provided therefor at the base or root of the member 30E to complete the connection.

FIG. 12 shows another embodiment which is somewhat similar to the construction shown in FIG. 3 except that the adjacent surfaces of the two flange portions 28F and 30F in this construction are grooved or serrated to prevent relative movements therebetween or shifting between the members after they have been joined. The construction shown in FIG. 12 like the FIG. 3 construction has a separate channel shaped closure member 92 which must be applied to hold the members together.

FIGS. 13 and 14 show other forms for the cooperating male and female closure means which are provided in some constructions to hold the members together. The construction shown in FIG. 13 has a sidewardly extending arrowhead shaped flange 32G which moves into and engages a similarly shaped groove 34G in the flange 30G. When these members are united they are not easily separated and will resist coming apart even under pressure. Note that the groove 34G is preferably intentionally made to be somewhat deeper than the cooperating head portion 32G on the flange 28G. This is done so that the member 32G can be pressed into the groove 34G far enough so that the edge portions 100 of the arrowhead shaped member 32G are able to clear edges or shoulders 102 of the groove 34G.

In FIG. 14 engagement is made between cooperating engageable means 32H and 34H. This construction like the arrowhead construction of FIG. 13 will resist coming apart under considerable pressure. Other forms of the cooperating means are also possible, and those shown are for illustrative purposes only.

FIGS. 15 and 16 show yet another embodiment wherein the mating surfaces of the flanges 28I and 30I are curved as at 110 and 112 so that when the members are united, as shown greatly exaggerated in FIG. 16, the edge portions 110 and 112 where they are attached to the skin will come together into firm abutment and may even be somewhat deformed to assure that the skin edges are held close together and in alignment during healing. This construction may offer the possibility of being somewhat more accurately applied to the edges of a skin separation since the abutting edges thereof may be somewhat easier to see since they project sidewardly, and therefore are easier to more accurately place along the edges of the skin separation.

FIG. 17 shows a construction similar to that shown in FIG. 10 but wherein a movable zipper closure assembly 120, used for opening and closing the closure means after being applied to the skin, is mounted as shown straddling the flanges 28D and 30D with the spaced curved side walls 122 of the movable zipper assembly 120 formed with inturned edge portions 124 which extend into grooves such as the grooves 38D formed at the roots of the flanges 28D and 30D, see FIGS. 2 and 10 for examples of such grooves. The movable zipper assembly 120 also has a separator portion 126 which moves between the flanges 28D and 30D to separate them when opening the closure means by moving the assembly 120 to the left as shown in FIG. 17. The side walls 122 on the other hand are curved or shaped to press the flanges 28D and 30D together and to unite them when the zipper assembly 120 is moved to the right. The zipper assembly 120 has an operator portion 128 which is the portion that is engaged by the one using it. The construction shown in FIG. 17, like the construction shown in FIG. 10, has an integral U-shaped closure wall portion 70 which is flexible enough to be easily moved out of the way to permit movement of the zipper assembly 120 therealong and can also be snapped into closed condition as shown in dotted outline in FIG. 10 when the zipper has completed uniting the closure means. It can therefore be seen that with the construction of FIG. 17 a person applying the subject device to an injury can close the members after they are adhesively applied, and can thereafter reopen the skin separation to inspect, apply medication or for some other reason.

It is also contemplated to make the portions 22 and 24 of the subject closures as wide or as narrow and as long and as short as required. If they are made relatively wide they will have greater adhesive attachment and hence greater pulling force, and if they are made relatively narrow they can be used on areas of the body where space is limited, such as for applying to forehead wounds near the brows and in other similar areas. Obviously, the members 22 and 24 can also be trimmed and shaped as desired. The subject devices may also be perforated or made of relatively porous materials to permit the escape of blood and other body fluids from the wound, and an absorbant padding can be applied over the subject closure means after they are applied to catch or absorb the escaping blood and other body fluids and to prevent soiling adjacent clothing and bed linens. All of this was disclosed in my U.S. Pat. No. 3,863,640.

FIG. 18 shows a roll 130 of the subject skin closure means which can be sterilized, placed in a sterilized container or dispenser or package and dispensed or cut off to the desired lengths as required in the usual manner for such devices. This is important for some applications especially where large quantities of the subject devices may be required such as in an operating room, in an emergency ward of a hospital, a disaster area where poeple are injured, in a battle field situation, and in other places where it is desired to be able to close a large number of wounds in a short period of time to prevent loss of blood and where suturing or stitching is too time consuming and where there is inadequate trained medical personnel. Even where there are adequate trained personnel the subject closures have a place because of the ease and accuracy with which they can be used and the fact that it presents or minimizes scar tissue formation. It is also contemplated to use the subject devices as the final closure means for operations such as for stomach or abdominal operations to mention only two of many possibilities. In these cases the surgeon may suture subcutaneously and then use the subject means for final skin closure. The roll 130 shown in FIG. 18 therefore represents an important and convenient way to package, handle and dispense the subject closure devices, and it is contemplated to maintain such rolls in sterile containers or packages at convenient locations. The present devices also have wide application for camping and other indoor and outdoor activities and circumstances where people may be injured, especially where it is not convenient or possible to get them to professional medical assistance in time to prevent scarring and loss of blood.

FIG. 19 shows another embodiment of the device which, when connected, makes a relatively smooth closure as compared to some of the other embodiments. In this case, the cooperation male and female means are formed on thickened edge portions 132 and 134 of the members to be joined, and these portions may have notches 136 and 138 which can be engaged by the fingernails or by a simple tool or closure member to bring them into engagement. This construction has the advantage of not being as able to catch on things as easily.

The construction shown in FIG. 20 is comparable to the structure of FIGS. 15 and 16 in that it provides means which operate to assure that the skin edges that are joined are held as close together as possible. This is accomplished in the FIG. 20 construction by providing an elongated bead or rib 140 along one of the flange members to be joined at a location on the opposite side of the engage means from the skin to apply a wedging or twisting action in a direction to hold the edges which are the edges attached to the skin together.

Thus there has been shown and described additional novel closure means for wounds, skin separations, incisions and other skin injuries and lacerations which fulfill all of the objects and advantages sought therefor. It will be apparent from this description however, that many other changes, modifications, variations, and other uses and applications for the subject closures, in addition to those that have been disclosed, are possible and contemplated. All such changes, modifications, variations and other uses and applications which do not depart from the spirit and scope of the invention are deemed to be covered by the invention which is limited only by the claims which follow.

What is claimed is:

1. Means for closing skin separations comprising a pair of sheet-like elements each having opposite side surfaces and adjacent side edges, an adhesive substance applied to corresponding side surfaces of each of said elements for attaching the elements to the skin adjacent to a skin separation with the side edges of said elements extending respectively along and closely adjacent to opposite sides of the skin separation, cooperating means on each of said sheet-like elements extending along the respective side edges thereof on the opposite sides thereof from the adhesive substance, the cooperating means and the adjacent sheet side edges on said elements being movable into abutment to close the skin separation, and elongated channel shaped means having continuous opposed edges extending substantially continuously the full length of the cooperating means cooperatively removably engaged with said cooperating means on said elements to hold said cooperating means together in abutment, said channel shaped means applying substantially uniform pressure to hold the elements together along the length of the engagement between the channel shaped means and the cooperating abuting means on the adjacent sheets.

2. The means defined in claim 1 wherein the elongated channel shaped means cooperatively engageable with said cooperating means include a channel shaped member having spaced side edge portions and a connecting wall portion extending therebetween, said channel shaped member being constructed and shaped to embrace the cooperating means when positioned in abutment.

3. The means defined in claim 2 wherein said channel shaped member is formed of relatively resilient material.

4. The means defined in claim 2 including means to separate at least a portion of the side edge portions of the channel shaped member to start to position it on the cooperating means.

5. The means defined in claim 1 wherein the cooperating means on the sheet-like elements have relatively flat surface portions which are in alignment with the side edges of the respective sheet-like elements, said cooperating means including elongated members of uniform cross-section being relatively thinner adjacent to where they are attached to the respective sheet-like elements.

6. The means defined in claim 5 wherein one of the elongated members has a sidewardly extending bead and the other of said elongated members has a groove formed extending into the side thereof, said groove being shaped to cooperatively receive the bead therein to hold the elongated members together.

7. The means defined in claim 6 wherein said sidewardly extending bead includes an elongated stem portion and an elongated head portion which is wider than the stem portion and is located on the opposite side of the stem portion from the one elongated member, the other of said elongated members being constructed of a relatively resilient material, the groove formed in said other elongated member having a cross-sectional shape similar to the cross-sectional shape of the stem and head portions of the said bead.

8. The means for closing skin separations defined in claim 6 wherein the side edges of said elongated members are shaped so that when the cooperating engageable means are engaged, portions of the side edges of the sheet-like elements adjacent to the adhesive substance are resiliently biased into engagement with each other.

9. The means defined in claim 6 including a movable member having a portion positioned bridging the cooperating means, said movable member including means to unite the cooperating means when moved in one direction therealong.

10. The means defined in claim 9 wherein the movable member includes means to separate the cooperating means when moved in an opposite direction therealong.

11. The means for closing skin separations defined in claim 1 wherein said cooperating engageable means include a resilient channel-shaped member formed of a stiff but resilient material having spaced connected leg portions for bridging and resiliently engaging and holding the cooperating means on said sheet-like members together, said channel-shaped member being integrally connected to one of the sheet-like elements and movable thereon between an inoperative position in which the cooperating means can be separated from each other and an operative position in which the channel-shaped member engages and holds the cooperating means together.

12. The means for closing skin separations defined in claim 1 wherein said pair of sheet-like elements are elongated members capable of being rolled up into a relatively compact roll.

13. Means for closing skin separations comprising a pair of separable members each having a side edge adapted to be moved into edge-to-edge abutment, said members having opposite surfaces corresponding ones of which have a surface layer of an adhesive thereon for attaching it to the skin, abutment means on each of said members on the opposite surface from the adhesive and extending along and contiguous to the said respective side edges to be moved into edge-to-edge abutment, and other means including an elongated closure member constructed of a stiff but somewhat resilient material, said closure member having continuous opposed edges being shaped and constructed to embrace the adjacent abutment means substantially along the full length of abutment of the abutment means on said members to hold the abutment means and the corresponding abutting edges of said members together.

14. The means defined in claim 13 wherein the abutment means on one of said members has a groove extending along the length thereof on the side that abuts the other abutment means, the other abutment means having means thereon for cooperative engagement with said groove to hold the members together in abutting relationship.

15. The means defined in claim 13 wherein said closure member includes a plurality of elongated connected wall portions and a pair of opposite side edges, one of said opposite side edges being integrally connected to one of said separable members adjacent to the abutment means thereon, the opposite side edge thereof being movable to a position wherein said connected wall portions embrace the abutment means and hold them together and in abutment.

16. The means defined in claim 13 wherein said abutment means have cooperative surface portions which engage each other to prevent relative movement therebetween when in abutment.

17. The means defined in claim 13 wherein said abutment means are elongated members having portions thereof that are narrower than other portions, said narrow portions of the abutment means being located adjacent to the respective separable member.

18. The means defined in claim 17 including a groove formed extending along at least one of said abutment means in position to cooperatively receive a portion of one of said side edges of the closure member to restrict relative movement thereof when positioned holding the abutment means together.

19. The means defined in claim 13 wherein the closure member is a tube shaped member having a lengthwise extending slit for forming an opening in one side thereof.

20. Means for closing a skin separation during healing comprising a bandage-like structure having first and second portions each including a strip portion having opposite surfaces and spaced side edges, a coating of an adhesive applied to corresponding surfaces of said portions for attaching the first portion to the skin extending along one side of the skin separation and attaching the second portion to the skin extending along the opposite side of the skin separation in spaced relationship to the first portion, said adhesive extending to the respective side edges of the first and second portions which are positioned to extend along opposite side edges of the skin separation, cooperatively engageable means respectively on said first and second portions on the side edges of the portions to be located extending along the respective side edges of the skin separation, said cooperatively engageable means including elongated flanges extending along the respective side edges of said portions, and means having continuous opposed edges removably engaging said flanges, said flange engaging means including a member formed of relatively stiff but resilient material extending along substantially the full length of the flanges to hold the flanges together.

* * * * *